(12) United States Patent
Zhang et al.

(10) Patent No.: US 11,897,830 B2
(45) Date of Patent: *Feb. 13, 2024

(54) CRYSTAL FORM AND AMORPHOUS FORM OF DEZOCINE ANALOGUE HYDROCHLORIDE

(71) Applicant: Shandong Danhong Pharmaceutical Co., Ltd., Shandong (CN)

(72) Inventors: Yang Zhang, Shanghai (CN); Wentao Wu, Shaghai (CN); Zhixiang Li, Shanghai (CN)

(73) Assignee: SHANDONG DANHONG PHARMACEUTICAL CO., LTD., Shandong (CN)

( * ) Notice: Subject to any disclaimer, the term of this patent is extended or adjusted under 35 U.S.C. 154(b) by 0 days.

This patent is subject to a terminal disclaimer.

(21) Appl. No.: 17/738,373

(22) Filed: May 6, 2022

(65) Prior Publication Data

US 2022/0259140 A1 Aug. 18, 2022

Related U.S. Application Data

(62) Division of application No. 16/611,926, filed as application No. PCT/CN2018/093721 on Jun. 29, 2018, now Pat. No. 11,339,119.

(30) Foreign Application Priority Data

Jul. 3, 2017 (CN) .......................... 201710532702.8

(51) Int. Cl.
*C07C 219/26* (2006.01)

(52) U.S. Cl.
CPC ........ *C07C 219/26* (2013.01); *C07B 2200/13* (2013.01); *C07C 2603/80* (2017.05)

(58) Field of Classification Search
CPC .............. C07C 219/26; C07C 2603/80; C07B 2200/13
USPC .......................................................... 560/44
See application file for complete search history.

(56) References Cited

U.S. PATENT DOCUMENTS

| | | | |
|---|---|---|---|
| 3,976,696 A | 8/1976 | Freed et al. |
| 3,979,434 A | 9/1976 | Freed et al. |
| 4,001,331 A | 1/1977 | Freed et al. |
| 4,034,041 A | 7/1977 | Freed et al. |

FOREIGN PATENT DOCUMENTS

| | | |
|---|---|---|
| CN | 102503840 A | 6/2012 |
| WO | 2017118375 A1 | 7/2017 |
| WO | 2018090982 A1 | 5/2018 |

OTHER PUBLICATIONS

English Translation of International Search Report for International Application No. PCT/CN2018/093721 dated Oct. 10, 2018.
Donohue et al., "Crystal and Molecular Structure of Analgesics. II. Dezocine Hydrobromide"—Department of Chemistry and Laboratory for Research on the Structure of Matter, Univ. of Pennsylvania, Jan. 5, 1981, pp. 69-78.

*Primary Examiner* — Ana Z Muresan
(74) *Attorney, Agent, or Firm* — CALFEE, HALTER & GRISWOLD LLP

(57) ABSTRACT

An amorphous form of dezocine analogue hydrochloride is represented by formula (II). An X-ray powder diffraction spectrum of the amorphous form is shown in FIG. 1.

5 Claims, 3 Drawing Sheets

CRYSTAL FORM AND AMORPHOUS FORM OF DEZOCINE ANALOGUE HYDROCHLORIDE

CROSS-REFERENCE TO RELATED APPLICATIONS

This application is a divisional of U.S. application Ser. No. 16/611,926, filed Nov. 8, 2019, which is the U.S. national phase entry of PCT/CN2018/093721, filed on Jun. 29, 2018, which claims the priority of Chinese patent application CN201710532702.8 filed on Jul. 3, 2017, the contents of which are hereby incorporated into the application.

TECHNICAL FIELD

The present invention relates to a crystal form and an amorphous form of dezocine analogue hydrochloride, and more particularly, to a crystal form of a compound represented by formula (I) and an amorphous form of a compound represented by formula (II).

BACKGROUND

Dezocine, with a chemical name of (−)-[5R-(5α,11α,13S*)]-13-amino-5,6,7,8,9,10,11,12-octahydro-5-methyl-5,11-methanobenzocyclodecen-3-ol, belongs to a typical opioid alkaloid analgesic developed by Swedish Astra Company. This kind of drugs plays a role by exciting an opioid receptor. Dezocine has a stronger analgesic effect than pentazocine, is a κ receptor agonist, and is also a μ receptor antagonist. Dezocine is less addictive and is suitable for treating moderate to severe pain after surgery, visceral colic and pain of patients with advanced cancer. Due to excellent tolerance and safety, dezocine is expected to become an opioid alkaloid analgesic with a good market prospect.

Dezocine has a structure as follows:

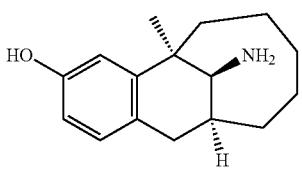

Different solid forms of pharmaceutical active ingredients may have different properties. Property changes of different solid forms can provide improved formulations, for example, ease of synthesis or handling, and improvement of stability and guarantee period. Property changes caused by different solid forms can also improve a final dosage form. Different solid forms of active pharmaceutical ingredients can also generate polycrystalline form or other crystal forms, thus providing more opportunities to evaluate the property changes of one solid active pharmaceutical ingredient.

TECHNICAL EFFECT

The crystal form of the compound represented by formula (I) and the amorphous form of the compound represented by formula (II) according to the present invention have simple preparation processes, and are relatively stable, less influenced by light and heat humidity, and convenient for preparation.

SUMMARY

In one aspect, the present invention provides a crystal form of a compound represented by formula (I),

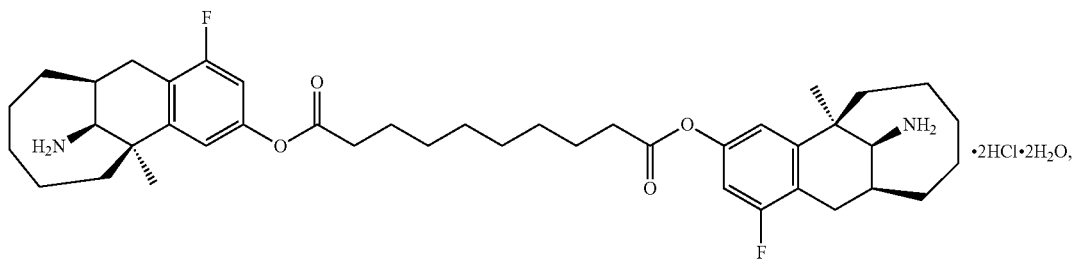

(I)

wherein an X-ray powder diffraction spectrum of the crystal form comprises characteristic peaks at 2θ values of 13.07°±0.2°, 16.84±0.2°, and 18.51±0.2°.

In some solutions of the present invention, the X-ray powder diffraction spectrum of the crystal form of the compound represented by formula (I) comprises characteristic peaks at 2θ values of 13.07°±0.2°, 15.30°±0.2°, 16.84°±0.2°, 18.51°±0.2°, 21.44°±0.2°, 23.18°±0.2°, 24.04°±0.2° and 26.20°±0.2.

In some solutions of the present invention, the X-ray powder diffraction spectrum of the crystal form of the compound represented by formula (I) is shown in FIG. 4.

In some solutions of the present invention, the X-ray powder diffraction spectrum of the crystal form of the compound represented by formula (I) is shown in FIG. 1.

TABLE 1

XRPD Diffraction Data of Crystal form of Compound Represented by Formula (I)

| No. | 2θ angle (°) | Interplanar distance (Å) | Relative intensity (%) |
|---|---|---|---|
| 1 | 12.415 | 7.1239 | 28.9 |
| 2 | 13.065 | 6.7708 | 100 |
| 3 | 14.05 | 6.2981 | 6.5 |
| 4 | 14.723 | 6.0118 | 21.7 |
| 5 | 15.061 | 5.8777 | 19.8 |
| 6 | 15.297 | 5.7875 | 28.5 |
| 7 | 16.073 | 5.5099 | 10.7 |
| 8 | 16.838 | 5.2611 | 38.7 |

TABLE 1-continued

XRPD Diffraction Data of Crystal form of
Compound Represented by Formula (I)

| No. | 2θ angle (°) | Interplanar distance (Å) | Relative intensity (%) |
|---|---|---|---|
| 9 | 17.364 | 5.1027 | 7.4 |
| 10 | 18.513 | 4.7886 | 57.2 |
| 11 | 19.581 | 4.5299 | 7.2 |
| 12 | 20.273 | 4.3766 | 24.6 |
| 13 | 20.686 | 4.2903 | 8.9 |
| 14 | 21.437 | 4.1416 | 29.7 |
| 15 | 22.033 | 4.031 | 21.5 |
| 16 | 23.016 | 3.8609 | 29.7 |
| 17 | 23.177 | 3.8345 | 43.1 |
| 18 | 24.044 | 3.6981 | 38.7 |
| 19 | 25.032 | 3.5544 | 10.8 |
| 20 | 25.395 | 3.5044 | 8.9 |
| 21 | 26.197 | 3.3989 | 45 |
| 22 | 27.914 | 3.1936 | 22.2 |
| 23 | 28.171 | 3.1651 | 14.5 |
| 24 | 30.546 | 2.9242 | 10.6 |

In some solutions of the present invention, a DSC curve of the crystal form of the compound represented by formula (I) comprises two endothermic peaks at 73.71° C.±3° C. and 245.82° C.±3° C.

In some solutions of the present invention, the DSC curve of the crystal form of the compound represented by formula (I) is shown in FIG. 5.

In some solutions of the present invention, when a TGA curve of the crystal form of the compound represented by formula (I) is at 120.00° C.±3° C., a weight is reduced by 5.812%; and when the TGA curve of the crystal form of the compound represented by formula (I) is at 200.12° C.±3° C., the weight is reduced by 6.5748%.

In some solutions of the present invention, the TGA curve of the crystal form of the compound represented by formula (I) is shown in FIG. 6.

In another aspect, the present invention provides an amorphous form of a compound represented by formula (II),

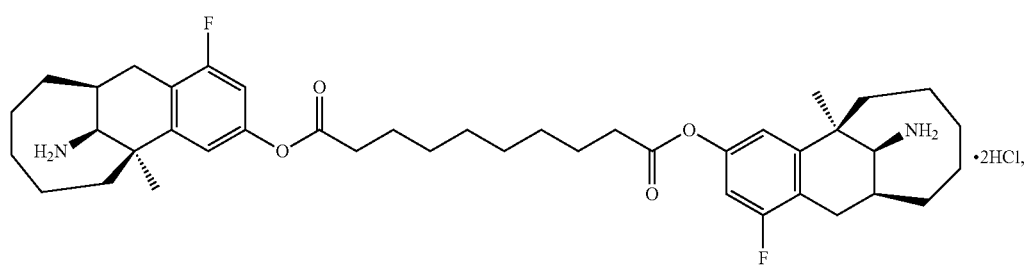

(II)

·2HCl, wherein an X-ray powder diffraction spectrum of the amorphous form is shown in FIG. 1.

In some solutions of the present invention, a MDSC curve of the amorphous form of the compound represented by formula (II) undergoes glass transition at 79.07° C.±3° C.

In some solutions of the present invention, the MDSC curve of the amorphous form of the compound represented by formula (II) is shown in FIG. 2.

In some solutions of the present invention, when a TGA curve of the compound represented by formula (II) is at 120.00° C., a weight is reduced by 4.270%; and when the TGA curve of the compound represented by formula (II) is at 199.60° C.±3° C., the weight is reduced by 5.1553%.

In some solutions of the present invention, the TGA curve of the compound represented by formula (II) is shown in FIG. 3.

Definition and Description

Unless otherwise stated, the following terms and phrases used herein are intended to have the following meanings. A specific term or phrase shall not be considered as being uncertain or unclear in case of no specific definitions, and shall be understood according to the ordinary meanings. Any commodity name herein is intended to refer to the corresponding commodity thereof or the active ingredients thereof.

The intermediate compounds of the present invention may be prepared by a variety of synthesis methods known by those skilled in the art, including the specific embodiments listed below, the embodiments formed by combination with other chemical synthesis methods, and equivalent replacements known by those skilled in the art. The preferred embodiments include but are not limited to the embodiments of the present invention.

The chemical reactions of the specific embodiments of the present invention are completed in suitable solvents, and the solvents must be suitable for the chemical changes of the present invention and the required reagents and materials. In order to obtain the compounds of the present invention, those skilled in the art sometimes need to modify or select the synthesis steps or reaction flows based on the existing embodiments.

The present invention will be described in detail below with reference to the embodiments, and the embodiments are not meant to limit the present invention in any way.

All the solvents used in the present invention are commercially available and may be used without further purification.

The solvents used in the present invention are commercially available.

The following abbreviations are used in the present invention:

DMF: N,N-dimethylformamide; Boc₂O: Boc anhydride; EDCI: 1-(3-dimethylaminopropyl)-3-ethylcarbodiimide hydrochloride; and DMAP: 4-dimethylaminopyridine.

Instrument and Analysis Method 1.1 X-Ray Powder Diffractometer (XRPD)

Instrument model: Bruker D8 advance X-ray diffractometer

Test method: about 10 mg to 20 mg of sample is used for XRPD detection.

Specific XRPD parameters are as follows:

light tube: Cu, kα (λ=1.54056 Å)

light tube voltage: 40 kV, light tube current: 40 mA divergence slit: 0.60 mm detector slit: 10.50 mm anti-scattering slit: 7.10 mm scanning scope: 4 deg to 40 deg step size: 0.02 deg step length: 0.12 s rotating speed of sample disk: 15 rpm 1.2 Differential Scanning Calorimeter (DSC)

Instrument model: TA Q2000 differential scanning calorimeter

Test method: a sample (~1 mg) is placed in a DSC aluminum pot for testing, and under the condition of 50 mL/min $N_2$, the sample is heated from a room temperature to 300° C. at a heating rate of 10° C./min.

1.3 Modulated Differential Scanning Calorimeter (MDSC)

Instrument model: TA Q2000 differential scanning calorimeter

Test method: a sample (~2 mg) is placed in a DSC aluminum pot for testing, and under the condition of 50 mL/min $N_2$, the sample is heated from 0° C. to 200° C. at a heating rate of 2° C./min, an amplitude of 1° C. and a period of 60 s.

1.4 Thermal Gravimetric Analyzer (TGA)

Instrument model: TA Q5000 thermal gravimetric analyzer

Test method: a sample (2 mg to 5 mg) is placed in a TGA platinum pot for testing, and under the condition of 25 mL/min $N_2$, the sample is heated from a room temperature to 20% weight loss at a heating rate of 10° C./min.

1.5 High Performance Liquid Chromatograph (HPLC)

Instrument model: Agilent 1200 high performance liquid chromatograph

The analysis method is as follows:

TABLE A

Determination Method for Content by HPLC Analysis

| Device | Agilent 1200 high performance liquid chromatograph |
|---|---|
| Chromatographic column | Waters-Xbridge C18 (150 mm × 4.6 mm, 3.5 μm) |
| Mobile phase A | 0.1% trifluoroacetic acid solution |
| Mobile phase B | 0.1% trifluoroacetic acid acetonitrile solution |
| Flow rate | 1.0 mL/min |
| Injection volume | 10.0 μL |
| Detection wavelength | 215 nm |
| Column temperature | 35° C. |
| Diluent | Acetonitrile: pure water 2/1 (v/v) |

| Gradient elution procedure | Time (min) | Mobile phase A (%) | Mobile phase B (%) |
|---|---|---|---|
| | 0.01 | 50 | 50 |
| | 5.00 | 20 | 80 |
| | 7.00 | 20 | 80 |
| | 7.01 | 50 | 50 |
| | 15.00 | 50 | 50 |

TABLE B

Determination Method for Related Substance by HPLC Analysis

| Device | Agilent 1200 high performance liquid chromatograph |
|---|---|
| Chromatographic column | Waters-Xbridge C18 (150 mm × 4.6 mm, 3.5 μm) |
| Mobile phase A | 0.1% trifluoroacetic acid solution |
| Mobile phase B | 0.1% trifluoroacetic acid acetonitrile solution |
| Flow rate | 1.0 mL/min |
| Injection volume | 10.0 μL |
| Detection wavelength | 215 nm |
| Column temperature | 35° C. |
| Diluent | Acetonitrile: pure water 2/1 (v/v) |

| Gradient elution procedure | Time (min) | Mobile phase A (%) | Mobile phase B (%) |
|---|---|---|---|
| | 0.00 | 80 | 20 |
| | 10.00 | 55 | 45 |
| | 40.00 | 0 | 100 |
| | 50.00 | 0 | 100 |
| | 50.01 | 80 | 20 |
| | 60.00 | 80 | 20 |

DETAILED DESCRIPTION

Figure 1:
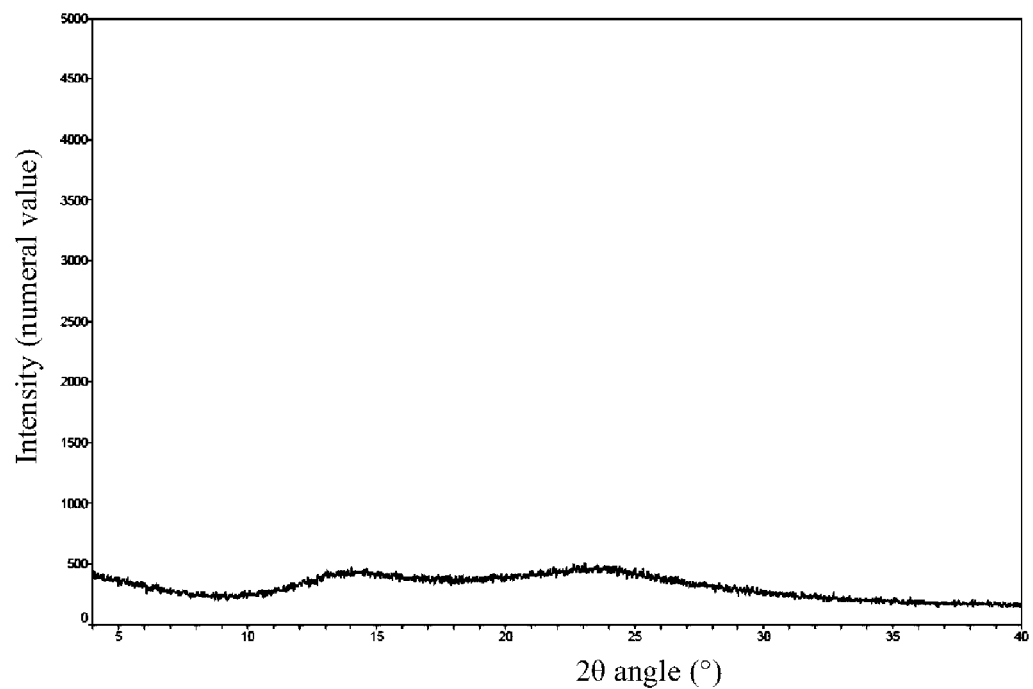
FIG. 1 is an XRPD spectrum of an amorphous form of a compound represented by formula (II).

The present invention will be described in detail hereinafter with reference to the embodiments, but it is not meant to be any disadvantageous limitation to the present invention. The present invention has been described in detail herein, and specific embodiments thereof have also been disclosed. It will be apparent to those skilled in the art that various changes and modifications can be made to the specific embodiments of the present invention without departing from the spirit and scope of the present invention.

Preparation of Embodiments

Preparation of Intermediate 1-3:

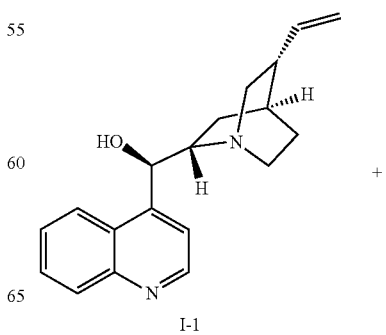

I-1

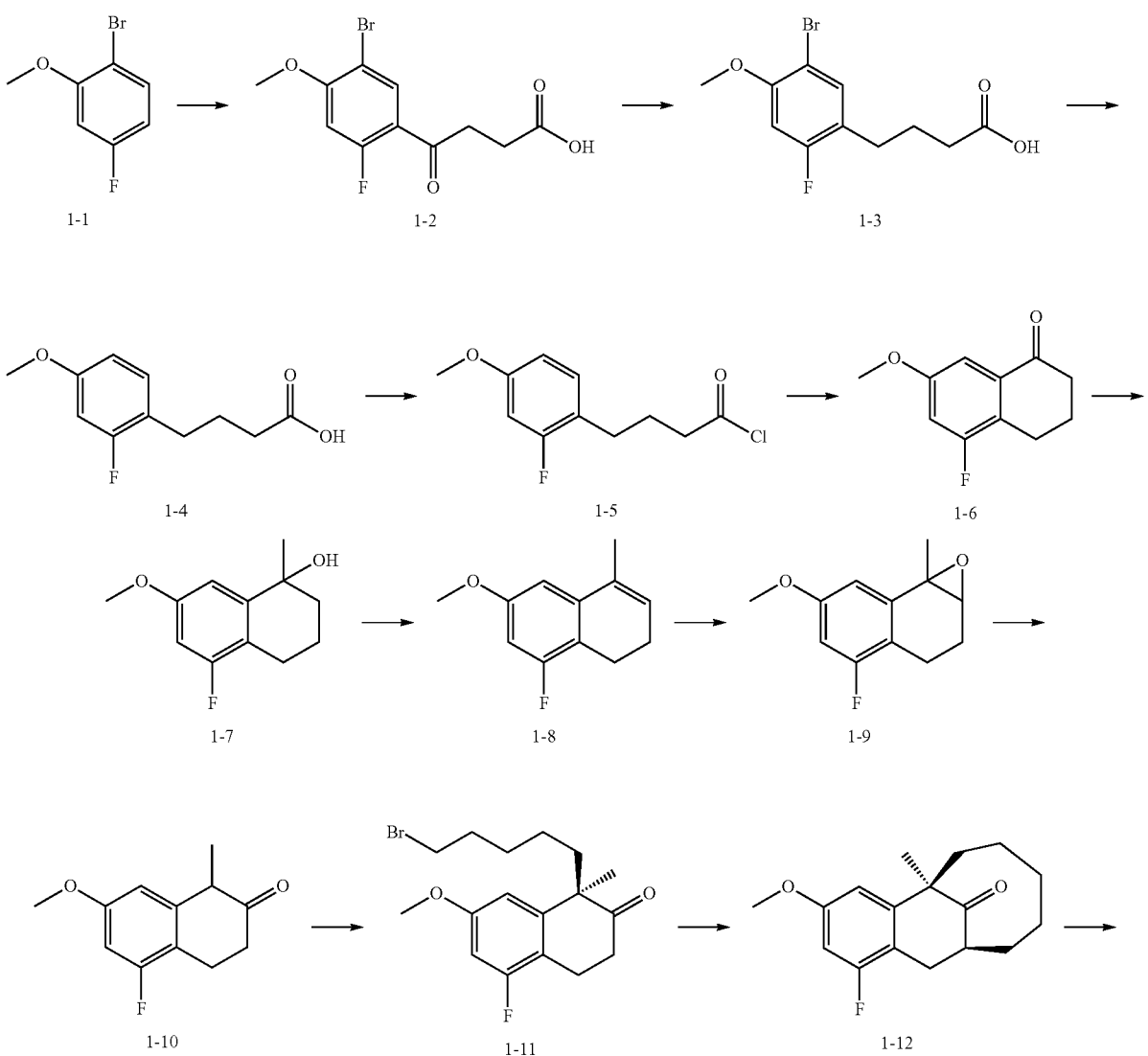

A compound I-1 (100.0 g, 339.69 mmol) and a compound I-2 (133.8 g, 509.54 mmol) were dissolved in anhydrous toluene (1.0 L), and the reaction solution was heated to 120° C. and continuously stirred for 16 h. After thermal filtration, the filtered solid was re-dispersed in 500 mL of toluene, the mixture was heated to reflux, thermally filtered, and dried in vacuum to obtain a compound I-3, and the compound was directly used in next reaction without further purification.

$^1$H NMR (400 MHz, CD$_3$OD): δ 8.98 to 8.97 (d, J=4.4 Hz, 1H), 8.46 (s, 2H), 8.32 to 8.27 (m, 2H), 8.19 to 8.15 (m, 1H), 7.99 to 7.98 (m, 1H), 7.88 to 7.82 (m, 2H), 6.67 (s, 1H), 5.75 to 5.66 (m, 1H), 5.47 to 5.42 (m, 1H), 5.20 to 5.16 (m, 2H), 5.05 to 5.02 (m, 1H), 4.62 to 4.60 (m, 1H), 4.08 to 4.05 (m, 1H), 3.75 to 3.65 (m, 1H), 3.52 to 3.46 (m, 1H), 3.43 to 3.40 (m, 1H), 2.76 (brs, 1H), 2.34 to 2.26 (m, 2H), 2.12 (brs, 1H), 1.95 to 1.90 (m, 1H), 1.49 to 1.44 (m, 1H); LCMS (ESI) m/z: 521.1 [M+1]$^+$.

Embodiment 1: Synthesis of Compound 1

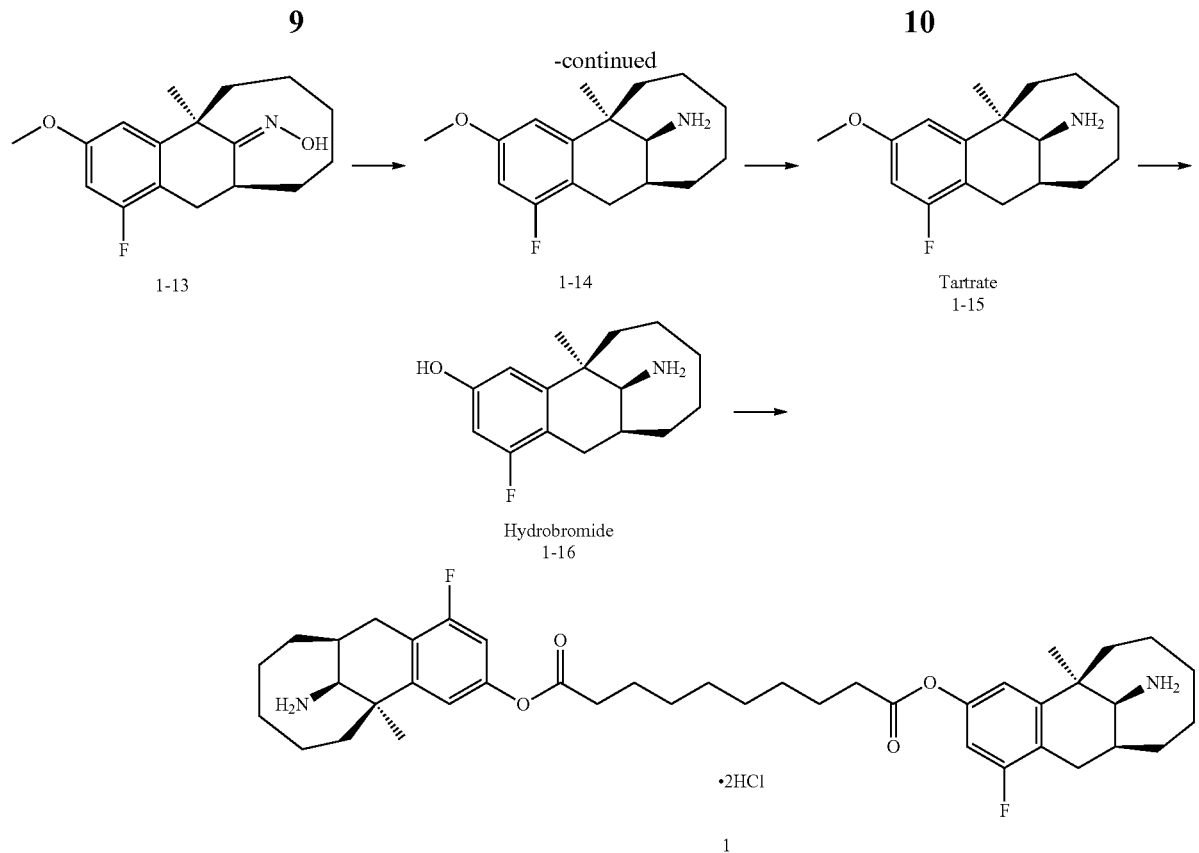

-continued 1-13

1-14

Tartrate
1-15

Hydrobromide
1-16

·2HCl

1

Step 1: Preparation of Compound 1-2

A compound 1-1 (5.0 kg, 24.58 mol) was added into anhydrous dichloromethane (31.0 L), then succinic anhydride (2.7 kg, 27.18 mol) and aluminum trichloride (6.7 kg, 50.32 mol) were added at once, and the reaction solution was continuously stirred at 20° C. to 25° C. for 20 h. The reaction solution was slowly poured into 60 L of ice water to stir and quench, then 1 L of concentrated hydrochloric acid was added to continuously stir the mixture for 5 min, and a large amount of white solids were generated. The mixture was filtered, and a filter cake was washed with 5 L of water and dried in vacuum to obtain a compound 1-2.

$^1$H NMR (400 MHz, CDCl$_3$): δ 8.19 to 8.16 (m, 1H), 6.69 to 6.66 (d, J=12.4 Hz, 1H), 3.98 (s, 3H), 3.30 to 3.26 (m, 2H), 2.82 to 2.79 (m, 2H). LCMS (ESI) m/z: 304.9 [M+1]$^+$.

Step 2: Preparation of Compound 1-3

The compound 1-2 (7.5 kg, 24.61 mol) was added into trifluoroacetic acid (8.9 kg, 78.52 mol, 5.81 L) at 20° C., triethyl silane (8.8 kg, 76.06 mol) was slowly added in batches, and a reaction solution was heated to 95° C. and continuously stirred for 16 h. The reaction solution was cooled to a room temperature, 10 L of petroleum ether was added, and a large amount of pink solids were precipitated. The mixture was filtered, and a filter cake was washed with 10 L of petroleum ether and dried in vacuum to obtain a compound 1-3.

$^1$H NMR (400 MHz, CD$_3$OD): δ 7.43 to 7.41 (d, J=8.0 Hz, 1H), 6.86 to 6.83 (d, J=11.6 Hz, 1H), 3.87 (s, 3H), 2.65 to 2.61 (t, J=7.6 Hz, 2H), 2.34 to 2.30 (t, J=7.6 Hz, 2H), 1.91 to 1.83 (m, 2H). LCMS (ESI) m/z: 290.8 [M+1]$^+$.

Step 3: Preparation of Compound 1-4

The compound 1-3 (1.1 kg, 3.92 mol) was dissolved in methanol (4.5 L) under an argon atmosphere, then wet palladium carbon (80.0 g, 10%) was added into a solution obtained, hydrogen replacement was conducted three times, and then the reaction solution was continuously stirred in a high pressure kettle at 50° C. for 48 h under 2.5 Mpa. The reaction solution was cooled down, and then taken out slowly; 500 mL of concentrated hydrochloric acid was added to stir until homogeneous, then the mixture was filtered, and a filter cake was washed with 2 L of methanol. The combined filter solution was adjusted with 50% sodium hydroxide solution to a pH was 10 to 11. An organic solvent was removed under reduced pressure, then the mixture was extracted twice with 4 L of ethyl acetate, and a combined organic phase was dried with anhydrous sodium sulfate and concentrated to obtain a crude compound 1-4, and the compound was directly used in next reaction without further purification.

$^1$H NMR (400 MHz, CD$_3$OD): δ 7.10 to 7.05 (m, 1H), 6.65 to 6.28 (m, 2H), 3.80 (s, 3H), 2.67 to 2.63 (t, J=7.2 Hz, 2H), 2.40 to 2.36 (t, J=7.6 Hz, 2H), 1.97 to 1.89 (m, 2H).

Step 4: Preparation of Compound 1-5

The compound 1-4 (596.0 g, 2.81 mol) was dissolved in anhydrous dichloromethane (2.0 L) at 15° C., 2 mL of anhydrous DMF was added, oxalyl chloride (427.8 g, 3.37 mol, 295.01 mL) was slowly added dropwise, and the reaction solution was continuously stirred at the temperature for 0.5 h. An organic solvent of the reaction solution was removed under reduced pressure, 200 mL of anhydrous dichloromethane was added into a crude product, an organic solvent was removed under reduced pressure, and a crude product compound 1-5 was directly used for next reaction without purification.

Step 5: Preparation of Compound 1-6

The crude product 1-5 (202.0 g, 875.75 mmol) was dissolved in anhydrous dichloromethane (4.0 L) at 25° C., powdery anhydrous aluminum trichloride (105.1 g, 788.17 mmol) was added at once, and the reaction solution was continuously stirred at 20° C. for 7 min. The reaction solution was poured into 1 L of ice water stirred, then the solution was separated, a water phase was extracted once with 1 L of dichloromethane, an organic phase was combined, an organic solvent was removed under reduced pressure, and an obtained crude product was separated and purified by silica gel column chromatography (petroleum ether:ethyl acetate=10:1 (v:v)) to obtain a compound 1-6.

$^1$H NMR (400 MHz, CDCl$_3$): δ 7.37 to 7.36 (d, J=2.4 Hz, 1H), 6.85 to 6.82 (m, 1H), 3.84 (s, 3H), 2.90 to 2.87 (t, J=6.4 Hz, 2H), 2.68 to 2.65 (t, J=6.4 Hz, 2H), 2.17 to 2.11 (m, 2H).

Step 6: Preparation of Compound 1-7

The compound 1-6 (1.0 kg, 5.15 mol) was dissolved in anhydrous toluene (4.0 L) under the protection of nitrogen, methylmagnesium bromide (3 M, 2.1 L, 5.15 mol) was added dropwise under the condition of ice-water bath, an internal temperature was kept not to exceed 10° C. during the dropwise adding process, and then the reaction solution was slowly heated to 25° C. and continuously stirred for 16 h. The reaction solution was poured into 4 L of saturated ammonium chloride solution, a liquid was separated, a water phase was extracted twice with 5 L of ethyl acetate, a combined organic phase was washed once with 3 L of saturated saline solution, an organic solvent was removed under reduced pressure to obtain a compound 1-7, and the compound was directly used in next reaction without further purification.

$^1$H NMR (400 MHz, CDCl$_3$): δ 6.98 to 6.97 (d, J=1.6 Hz, 1H), 6.56 to 6.53 (m, 1H), 3.87 (s, 3H), 2.70 to 2.67 (m, 2H), 1.99 to 1.80 (m, 4H), 1.56 (s, 3H).

Step 7: Preparation of Compound 1-8

The crude product 1-7 (1.8 kg, 8.75 mol) was dissolved in acetonitrile (1.0 L) at 25° C., 6 N hydrochloric acid (2.5 L) was added, and the reaction solution was continuously stirred for 16 h. 4 L of ethyl acetate was added, a liquid was separated, a water phase was extracted for three times with 5 L of ethyl acetate, a combined organic phase was washed with 3 L of saturated saline solution, an organic solvent was removed under reduced pressure to obtain a crude product 1-8, and the compound was directly used in next reaction without further purification.

$^1$H NMR (400 MHz, CDCl$_3$): δ 6.63 to 6.62 (d, J=2.0 Hz, 1H), 6.51 to 6.48 (m, 1H), 5.93 to 5.90 (m, 1H), 3.80 (s, 3H), 2.73 to 2.69 (t, J=8.0 Hz, 2H), 2.25 to 2.22 (m, 2H), 2.04 to 2.03 (d, J=3.2 Hz, 3H).

Step 8: Preparation of Compound 1-9

The compound 1-8 (493.0 g, 2.56 mol) was dissolved in a mixed solvent of acetone (2.0 L) and water (2.0 L) at 25° C., sodium bicarbonate (861.8 g, 10.26 mol) was added, then potassium peroxymonosulfate (1.0 kg, 1.67 mol) was slowly added in batches, an internal temperature was controlled not to exceed 30° C. during the adding process, and the reaction solution was continuously stirred at the temperature for 1.5 h. 2 L of saturated sodium sulfite solution was slowly added into the reaction solution, a test by starch potassium iodide paper showed no color change to blue, the mixture was placed still, a supernatant was taken out, the solid was washed with 1.5 L of dichloromethane for three times, the supernatant and the dichloromethane cleaning solution were combined, a liquid was separated, a water phase was extracted with 6 L of dichloromethane, a combined organic phase was washed with 6 L of saturated saline solution and dried with anhydrous sodium sulfate, the solution was filtered and concentrated under reduced pressure, tests by starch potassium iodide paper showed no color change to blue in the concentration process, a crude product 1-9 was obtained, and the compound was directly used in next reaction without further purification.

Step 9: Preparation of Compound 1-10

The crude compound 1-9 (450.0 g, 2.16 mol) was dissolved in anhydrous dichloromethane (3.0 L) at 0° C., an anhydrous dichloromethane (100 mL) solution of a boron trifluoride etherate complex (30.7 g, 216.00 mmol, 26.67 mL) was slowly added dropwise into an obtained solution, and a reaction solution was continuously stirred for 30 min. The reaction solution was slowly poured into 1.5 L of saturated sodium carbonate solution, an organic phase was separated, a water phase was extracted twice with 1.5 L of dichloromethane, a combined organic phase was washed with 2 L of saturated saline solution and dried with anhydrous sodium sulfate, the solution was filtered, an organic solvent was removed under reduced pressure, and an obtained crude product was separated and purified by silica gel column chromatography (petroleum ether:ethyl acetate=15:1 (v:v)) to obtain a compound 1-10.

$^1$H NMR (400 MHz, CDCl$_3$): δ 6.59 to 6.52 (m, 2H), 3.79 (s, 3H), 3.49 to 3.47 (m, 1H), 3.14 to 3.10 (m, 1H), 2.99 to 2.85 (m, 1H), 2.58 to 2.48 (m, 2H), 1.46 to 1.44 (d, J=7.6 Hz, 3H).

Step 10: Preparation of Compound 1-11

The compound 1-10 (448.0 g, 2.15 mol) and 1,5-dibromopentane (1.5 kg, 6.45 mol) were dissolved in a mixed solvent of toluene (30.0 L) and dichloromethane (3.0 L), then the compound 1-3 (119.8 g, 215.00 mmol) was added, 50% potassium hydroxide solution (3.0 L) was slowly and dropwise added under a nitrogen atmosphere, and a reaction solution was heated to 15° C. and continuously stirred for 20 h. 6 L of saturated saline solution was added, a liquid was separated, a water phase was extracted with 6 L of ethyl acetate, an organic solvent was removed from a combined organic phase under reduced pressure, and an obtained crude product was separated and purified by silica gel column chromatography (petroleum ether:ethyl acetate=20:1 (v:v)) to obtain a compound 1-11.

$^1$H NMR (400 MHz, CDCl$_3$): δ 6.63 to 6.62 (d, J=2.0 Hz, 1H), 6.56 to 6.53 (m, 1H), 3.81 (s, 3H), 3.34 to 3.30 (t, J=7.2 Hz, 2H), 3.14 to 3.10 (m, 1H), 2.95 to 2.85 (m, 1H), 2.65 to 2.57 (m, 2H), 2.23 to 2.08 (m, 1H), 1.77 to 1.73 (m, 2H), 1.70 to 1.58 (m, 1H), 1.39 (s, 3H), 1.34 to 1.30 (m, 2H), 0.97 to 0.94 (m, 2H).

An ee value of the compound was 58.7%, where the RRT were 1.782 and 1.954 respectively.

Step 11: Preparation of Compound 1-12

The compound 1-11 (1.1 kg, 3.05 mol) was dissolved in dimethyl sulfoxide (7.0 L) at 0° C., sodium tert-butoxide (351.8 g, 3.66 mol) was slowly added in batches, an internal temperature was kept not to exceed 30° C., and a reaction solution was continuously stirred for 30 min. The reaction solution was slowly poured into 6 L of ice water, 6 L of ethyl acetate was added, a liquid was separated, a water phase was extracted with 20 L of ethyl acetate, a combined organic phase was washed with 20 L of saturated saline solution, an organic solvent was removed under reduced pressure, and a crude product was separated and purified by silica gel column chromatography (petroleum ether:ethyl acetate=20:1 (v:v)) to obtain a compound 1-12.

$^1$H NMR (400 MHz, CDCl$_3$): δ 6.54 to 6.53 (d, J=2.0 Hz, 1H), 6.47 to 6.43 (m, 1H), 3.72 (s, 3H), 3.02 to 2.98 (m, 1H), 2.86 to 2.80 (m, 1H), 2.70 to 2.68 (m, 1H), 2.35 to 2.25 (m, 1H), 1.81 to 1.78 (m, 1H), 1.71 to 1.68 (m, 2H), 1.52 to 1.47 (m, 4H), 1.27 (s, 3H), 1.26 to 1.23 (m, 2H).

Step 12: Preparation of Compound 1-13

The compound 1-12 (882.0 g, 3.19 mol) was dissolved in ethanol (3.0 L), then pyridine (2.5 kg, 31.92 mol, 2.58 L) and hydroxylamine hydrochloride (2.2 kg, 31.92 mol) were added into an obtained solution, and the reaction solution was heated to 100° C. and continuously stirred for 24 h. The reaction solution was poured into 6 L of ethyl acetate, 4 L of water was added, a liquid was separated, a water phase was extracted twice with 4 L of ethyl acetate, a combined organic phase was washed with 4 L of hydrochloric acid (4N), washed with 4 L of saturated saline solution and dried with anhydrous sodium sulfate, an organic solvent was removed under reduced pressure to obtain a crude product 1-13, and the compound was directly used in next reaction without further purification.

1H NMR (400 MHz, CDCl$_3$): δ 6.57 to 6.56 (d, J=1.6 Hz, 1H), 6.44 to 6.39 (m, 1H), 3.74 to 3.66 (m, 4H), 2.88 to 2.84 (m, 1H), 2.78 to 2.76 (m, 1H), 2.21 to 2.20 (m, 1H), 2.08 to 2.03 (m, 1H), 1.56 to 1.48 (m, 6H), 1.46 (s, 3H), 1.45 to 1.40 (m, 2H).

Step 13: Preparation of Compound 1-14

The compound 1-13 (404.0 g, 1.39 mol) was dissolved in methanol (7.0 L), ammonia water (130.3 g, 929.02 mmol, 143.13 mL) was added, Raney nickel (377.8 g, 2.20 mol) was added under an argon atmosphere, hydrogen replacement was conducted three times, and the reaction solution was continuously stirred in a high pressure kettle with 3 Mpa hydrogen at 80° C. to 85° C. for 72 h. The reaction solution was cooled to a room temperature and filtered under an argon atmosphere, a filter cake was washed with 1 L of methanol, an organic solvent was removed under reduced pressure to obtain a crude product 1-14, and the compound was directly used in next reaction without further purification.

$^1$H NMR (400 MHz, CDCl$_3$): δ 6.57 to 6.56 (d, J=1.6 Hz, 1H), 6.44 to 6.39 (m, 1H), 3.74 to 3.66 (m, 4H), 2.88 to 2.84 (m, 1H), 2.78 to 2.76 (m, 1H), 2.21 to 2.20 (m, 1H), 2.08 to 2.03 (m, 1H), 1.56 to 1.48 (m, 6H), 1.46 (s, 3H), 1.45 to 1.40 (m, 2H).

Step 14: Preparation of Compound 1-15

The compound 1-14 (756.0 g, 2.73 mol) was dissolved in a mixed solution of ethyl acetate (750 mL) and methanol (2.3 L), then D-tartaric acid (250.0 g, 1.67 mol) was added into the mixed solution, the reaction solution was heated to 80° C. to 85° C. and continuously stirred for 1 h, white solid was generated, water (750 mL) was added, and the reaction solution was continuously stirred at 80° C. to 85° C. for 2 h, slowly cooled to a room temperature and placed still for 24 h. The reaction solution was filtered, and a filter cake was washed with 1 L of ethyl acetate and dried in vacuum to obtain tartrate of the compound 1-15.

$^1$H NMR (400 MHz, CD$_3$OD): δ 6.67 to 6.66 (m, 1H), 6.63 to 6.60 (m, 1H), 4.40 (s, 2H), 3.78 (s, 3H), 3.68 to 3.65 (m, 1H), 2.93 to 2.90 (m, 2H), 2.56 to 2.54 (m, 1H), 1.97 to 1.85 (m, 2H), 1.78 to 1.70 (m, 2H), 1.61 to 1.57 (m, 3H), 1.49 (s, 3H), 1.21 to 1.18 (m, 1H), 0.90 to 0.84 (m, 2H). LCMS (ESI) m/z: 278.1 [M+1]$^+$.

An ee value of the compound was 99.1%, where the RRT were 2.726 and 3.205 respectively.

Step 15: Preparation of Compound 1-16

The compound 1-15 (162.0 g, 378.98 mmol) was added into 40% hydrobromic acid solution (710 mL), and the reaction solution was heated to 120° C. and continuously stirred for 72 h. The reaction solution was cooled and filtered, and a filter cake was washed with 1.5 L of water and dried in vacuum to obtain hydrobromide of the compound 1-16.

$^1$H NMR (400 MHz, CD$_3$OD): δ 6.67 to 6.66 (d, J=0.8 Hz, 1H), 6.47 to 6.43 (m, 1H), 3.69 to 3.67 (m, 1H), 2.93 to 2.90 (m, 2H), 2.57 to 2.55 (m, 1H), 1.98 to 1.92 (m, 2H), 1.79 to 1.59 (m, 5H), 1.48 (s, 3H), 1.24 to 1.21 (m, 1H), 0.92 to 0.89 (m, 2H). LCMS (ESI) m/z: 264.0 [M+1]$^+$.

An ee value of the compound was 99.5%, where the RRT were 3.228 and 3.966 respectively.

Step 16: Preparation of Compound 1-17

The compound 1-16 (170.1 g, 494.05 mmol) was dissolved in anhydrous tetrahydrofuran (1200 mL), triethylamine (104.0 mL, 750.3 mmol) was added, (Boc)$_2$O (108.2 g, 495.81 mmol) was slowly added dropwise, and the reaction solution was continuously stirred at 30° C. for 16 h. The reaction solution was poured into 2 L of water and extracted with 800 mL of ethyl acetate, a liquid was separated, and a water phase was extracted twice with 800 mL of ethyl acetate. A combined organic phase was washed with 1 L of saturated saline solution and dried with anhydrous sodium sulfate, and an organic solvent was removed under reduced pressure. A crude product was heated and dispersed in 1200 mL of mixed solvent of n-heptane and ethyl acetate (5:1 (v:v)), the mixture was placed still overnight and filtered, and a filter cake was dried in vacuum to obtain a compound 1-17.

$^1$H NMR (400 MHz, CD$_3$OD): δ 6.52 to 6.51 (d, J=1.2 Hz, 1H), 6.39 to 6.34 (m, 1H), 4.04 to 4.00 (m, 1H), 2.89 to 2.76 (m, 2H), 2.30 to 2.29 (m, 1H), 1.83 to 1.71 (m, 4H), 1.58 to 1.51 (m, 12H), 1.28 to 1.26 (m, 4H), 0.96 to 0.90 (m, 2H). LCMS (ESI) m/z: 308.0 [M to 56+1]$^+$.

Step 17: Preparation of Compound 1-18

The compound 1-17 (155.1 g, 426.72 mmol) was added into anhydrous dichloromethane (2.0 L), DMAP (26.1 g, 213.36 mmol), decanedioic acid (43.2 g, 213.36 mmol) and EDCI (106.3 g, 554.73 mmol) were added in sequence, and the reaction solution was continuously stirred at 30° C. for 16 h. The reaction solution was poured into 2 L of water, a liquid was separated, and a water phase was extracted twice with 850 mL of dichloromethane. A combined organic phase was washed with 1.5 L of saturated saline solution and dried with anhydrous sodium sulfate, an organic solvent was removed under reduced pressure, and a crude product was separated and purified by silica gel column chromatography (petroleum ether:ethyl acetate=10:1-3:1 (v:v)) to obtain a compound 1-18.

$^1$H NMR (400 MHz, CDCl$_3$): δ 6.76 (s, 2H), 6.71 to 6.69 (m, 2H), 4.96 to 4.93 (d, J=10.4 Hz, 2H), 4.13 to 4.09 (m, 2H), 2.96 to 2.85 (m, 4H), 2.58 to 2.54 (t, J=7.6 Hz, 1H), 2.42 (brs, 2H), 1.79 to 1.51 (m, 31H), 1.49 to 1.28 (m, 21H), 0.96 to 0.90 (m, 4H). LCMS (ESI) m/z: 893.6 [M+1]$^+$.

Step 18: Preparation of Compound 1

The compound 1-18 (120.0 g, 134.39 mmol) was dissolved in ethyl acetate (410 mL), an ethyl acetate solution of 4 M hydrogen chloride (500 mL) was added at once, and the reaction solution was continuously stirred at a room temperature for 2 h until no gas was generated. The reaction solution was filtered under a nitrogen atmosphere, and a filter cake was washed with 300 mL of ethyl acetate and dried in vacuum to obtain hydrochloride of the compound 1.

$^1$H NMR (400 MHz, CD$_3$OD): δ 6.83 (s, 2H), 6.73 to 6.71 (m, 2H), 4.03 to 4.00 (m, 2H), 2.93 to 2.89 (m, 4H), 2.52 to 2.49 (m, 6H), 1.90 to 1.86 (m, 4H), 1.69 to 1.63 (m, 8H), 1.52 to 1.49 (m, 6H), 1.41 (s, 6H), 1.40 to 1.33 (m, 8H), 1.18 to 1.12 (m, 2H), 0.79 to 0.72 (m, 4H). LCMS (ESI) m/z: 693.5 [M+1]$^+$.

Chiral analysis methods for the compound 1-11 and the compound 1-15 are shown in Table C below:

TABLE C

Chiral Analysis Methods for Compound 1-11 and Compound 1-15

| Device | Supercritical liquid chromatograph equipped with ultraviolet detector |
|---|---|
| Chromatographic column | Chiralpak AY-3 150 × 4.6 mm I.D., 3 μm |
| Mobile phase A | Supercritical carbon dioxide |
| Mobile phase B | Ethanol (containing 0.05% diethylamine) |
| Flow rate | 2.5 mL/min |
| Detection wavelength | 220 nm |
| Column temperature | 35° C. |
| Diluent | Methanol |

| Gradient elution procedure | Time (min) | Mobile phase A (%) | Mobile phase B (%) |
|---|---|---|---|
| | 0.00 | 95 | 5 |
| | 5.00 | 60 | 40 |
| | 7.50 | 60 | 40 |
| | 7.51 | 95 | 5 |
| | 10.00 | 95 | 5 |

A chiral analysis method for the compound 1-16 is shown in Table D below:

TABLE D

Chiral Analysis Method for Compound 1-16

| Device | Supercritical liquid chromatograph equipped with ultraviolet detector |
|---|---|
| Chromatographic column | Chiralpak AD-3 100 × 4.6 mm I.D., 3 μm |
| Mobile phase A | Supercritical carbon dioxide |
| Mobile phase B | Ethanol (containing 0.05% diethylamine) |
| Flow rate | 2.8 mL/min |
| Detection wavelength | 280 nm |
| Column temperature | 40° C. |
| Diluent | Methanol |

| Gradient elution procedure | Time (min) | Mobile phase A (%) | Mobile phase B (%) |
|---|---|---|---|
| | 0.00 | 95 | 5 |
| | 4.50 | 60 | 40 |
| | 7.00 | 60 | 40 |
| | 7.01 | 95 | 5 |
| | 8.00 | 95 | 5 |

Embodiment 2: Preparation of Amorphous Form Sample of Compound Represented by Formula (II)

An appropriate amount of raw material compound 1 was added into an agate mortar and grinded for 60 min to obtain the sample.

Figure 2:
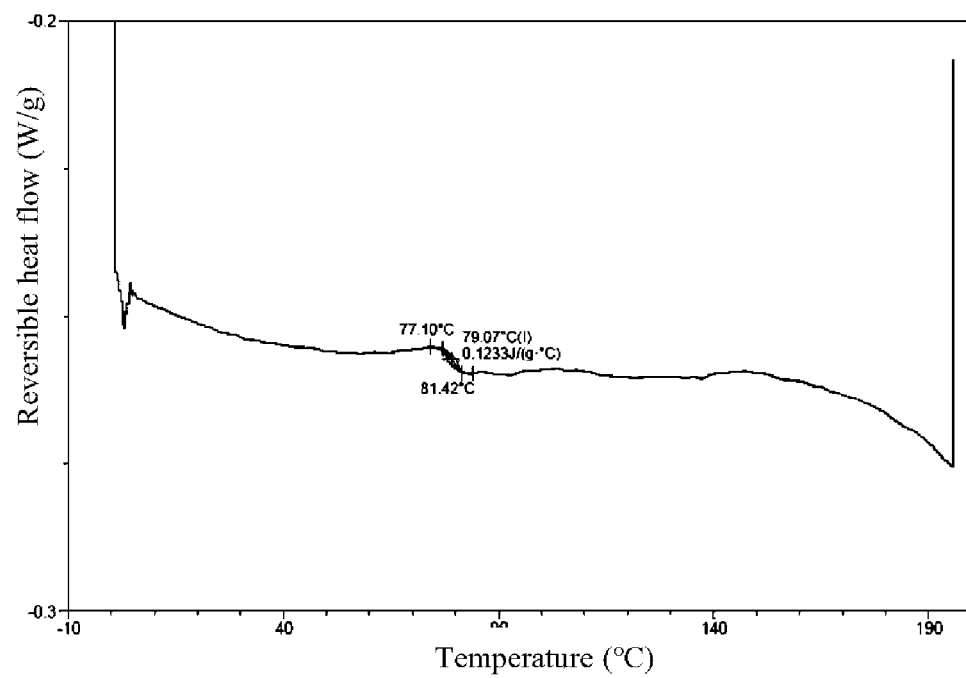
FIG. 2 is a MDSC spectrum of the amorphous form of the compound represented by formula (II).
Figure 3:
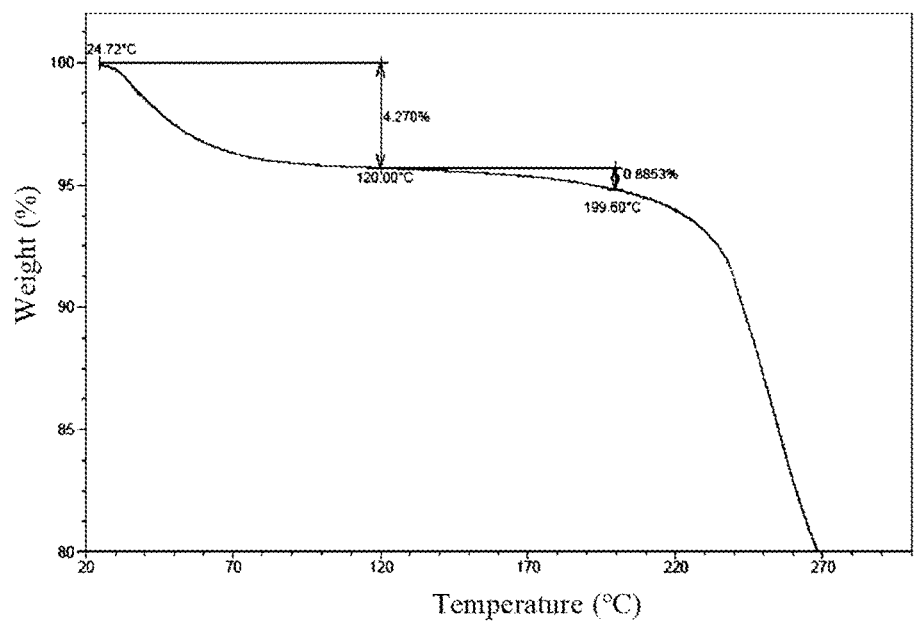
FIG. 3 is a TGA spectrum of the amorphous form of the compound represented by formula (II).

An XRPD detection result is shown in FIG. 1, and MDSC and TGA detection results are shown in FIGS. 2 and 3.

Embodiment 3: Preparation of Crystal Form Sample of Compound Represented by Formula (I)

200 mg of raw material compound 1 was added into 2.0 mL of acetonitrile-water mixed solvent (90:10, v:v). The mixture was magnetically stirred at 37° C. for 2 days, and after centrifugation, a residual solid sample was placed in a vacuum drying oven (35° C.) and dried for 3 days.

Figure 4:
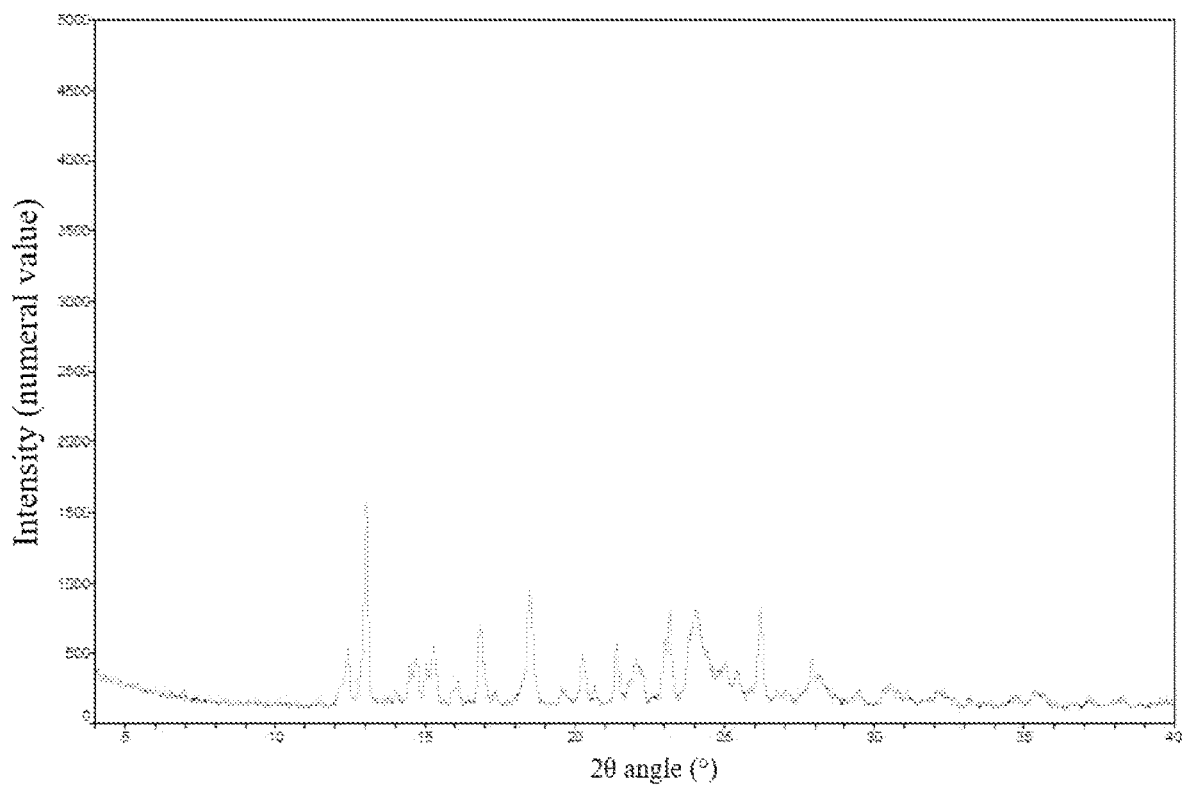
FIG. 4 is an XRPD spectrum of a crystal form of a compound represented by formula (I).
Figure 5:
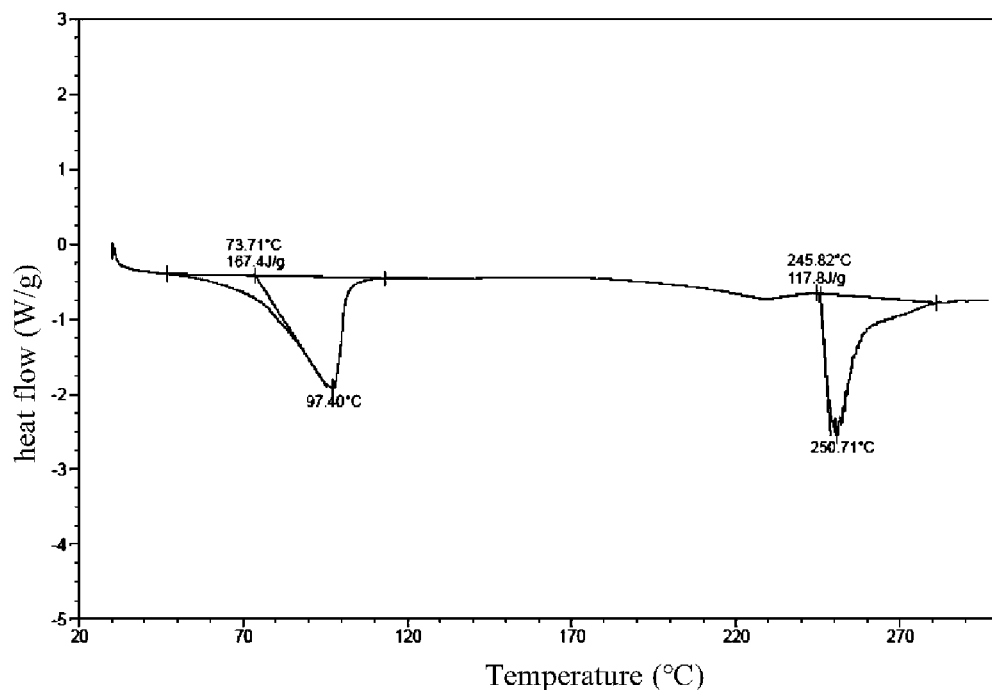
FIG. 5 is a DSC spectrum of the crystal form of the compound represented by formula (I).
Figure 6:
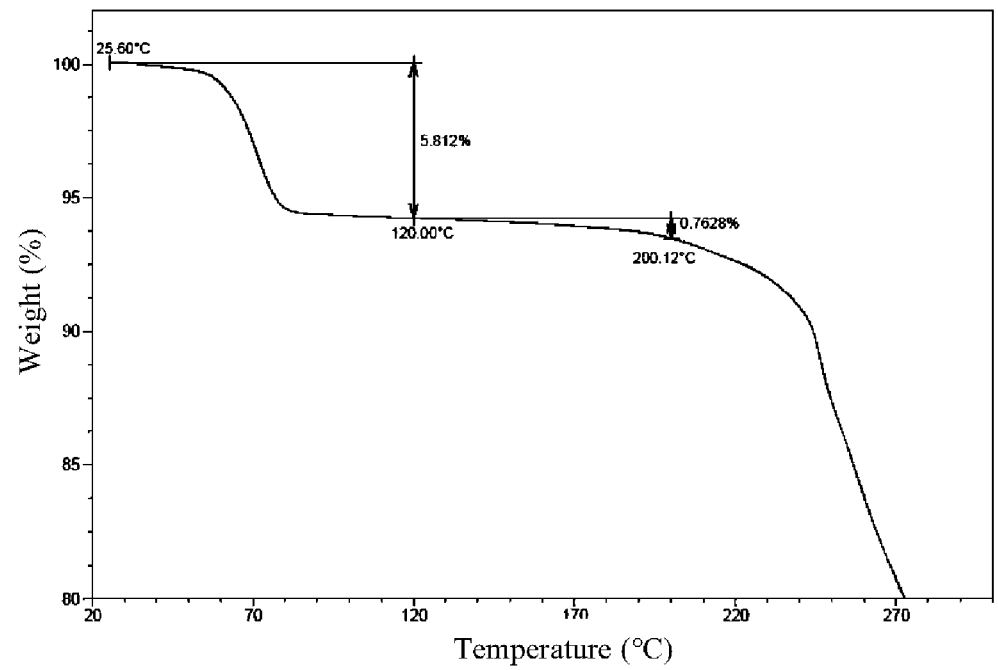
FIG. 6 is a TGA spectrum of the crystal form of the compound represented by formula (I).

An XRPD detection result is shown in FIG. 4 and Table 1, and DSC and TGA detection results are shown in FIGS. 5 and 6.

Characterization of Embodiments

Embodiment 1: Solid Stability Test

1. Solid Stability Test of Crystal Form of Compound Represented by Formula (I)

According to the Guiding Principles for Stability Experiment of Crude Drugs and Preparations (General Rules 9001 of Chinese Pharmacopoeia (2015 Version) Volume IV), a stability of a compound placed under conditions of high temperature (60° C., open), high humidity (RT/92.5% RH, open) and illumination (5000lx, closed) for 5 days and 10 days were investigated.

An appropriate amount of a crystal form sample of a compound represented by formula (I) was placed at a bottom of a glass sample bottle and spread into a thin layer. The sample placed under the conditions of high temperature and high humidity was sealed with aluminum-foil paper, and small holes were punched in the aluminum-foil paper to ensure that the sample could be fully contacted with ambient air. The sample placed under the condition of illumination (5000lx) was sealed with a bottle cap and further sealed with a sealing film, the sample was sealed and placed at a room temperature, and XRPD detection was performed on the 5$^{th}$ day and the 10$^{th}$ day. The detection results were compared with an initial detection result of 0 day, all crystal forms of result samples did not change, and the test results are shown in Table 2 below.

TABLE 2

Solid Stability Test of Crystal Form of Compound Represented by Formula (I)

| Test condition | Time point | Crystal form (XRPD) |
|---|---|---|
| — | 0 day | Crystal form of compound represented by formula (I) |
| High temperature (60° C., open) | 5 days | Crystal form of compound represented by formula (I) |
|  | 10 days | Crystal form of compound represented by formula (I) |
| High humidity (RT/RH 92.5%, open) | 5 days | Crystal form of compound represented by formula (I) |
|  | 10 days | Crystal form of compound represented by formula (I) |
| Illumination (5000lx, closed) | 5 days | Crystal form of compound represented by formula (I) |
|  | 10 days | Crystal form of compound represented by formula (I) |

The result showed that the crystal form of the compound was stable under the conditions of high temperature, high humidity and illumination without any change.

2. Solid Stability Test of Amorphous Form of Compound Represented by Formula (II)

Stability of amorphous form sample under conditions of high temperature, high humidity (40° C./RH 75.0%, closed) and acceleration.

About 1.4 g of sample was put into a double-layer LDPE bag, each layer of LDPE bag was fastened and sealed respectively, then the LDPE bag and a medicinal desiccant were put into an aluminum-foil bag and sealed by heating, under conditions of high temperature and high humidity, a sample was taken on the $30^{th}$ day for detection, and a detection result was compared with an initial detection result on the $0^{th}$ day. The test result is shown in Table 3.

TABLE 3

Solid Stability Test of Amorphous Form of Compound Represented by Formula (II)

| Test condition | Time point | Content (%) | Total impurity (%) |
|---|---|---|---|
| — | 0 day | 99.3 | 1.56 |
| High temperature and high humidity (40° C./RH 75.0%, close) | 30 days | 97.8 | 1.96 |

The result showed that the amorphous form solid of the compound was relatively stable under the conditions of high temperature, high humidity and sealing, and the total impurity did not increase significantly.

3. Solubility Experiment of Amorphous Form Sample of Compound Represented by Formula (II)

An equilibrium solubility of an amorphous form sample in pH 1.0/2.0 (hydrochloric acid solution), pH 3.8/4.5/5.5 (acetate buffer solution), pH 6.0/6.8/7.4 (phosphate buffer solution) and water was detected (prepared according to the Technical Guiding Principles for Dissolution Rate Test of Ordinary Oral Solid Preparations of Chinese Pharmacopoeia).

5 mL of different media (pH 1.0, pH 2.0, pH 3.8, pH 4.5, pH 5.5, pH 6.0, pH 6.8 and pH 7.4 buffer solutions and pure water) were respectively added into nine 8 mL glass bottles, and an appropriate amount of amorphous form sample was added respectively to make the mixture a suspension. Magnetic stirring bars were added into the sample above, which are placed on a magnetic stirrer to stir (at a temperature of 37° C.).

The sample was centrifuged after 24 h, and a supernatant was taken from an upper sample to determine a concentration thereof by HPLC and a pH value thereof (results shown in Table 4).

TABLE 4

Solubility Result of Amorphous Form Sample of Compound Represented by Formula (II) in Different pH Media

| Menstruum | pH | State | Solubility (mg/mL) 24 h |
|---|---|---|---|
| 0.1N HCl | 1.02 | Turbid | 0.398 |
| 0.01N HCl | 2.01 | Turbid | 1.629 |
| pH 3.8 buffer solution | 3.68 | Turbid | 15.097 |
| pH 4.5 buffer solution | 4.48 | Turbid | 19.637 |
| pH 5.5 buffer solution | 5.25 | Turbid | 18.723 |
| pH 6.0 buffer solution | 5.89 | Turbid | 0.013 |
| pH 6.8 buffer solution | 6.75 | Turbid | 0.003 |
| pH 7.4 buffer solution | 7.20 | Turbid | <LOQ |
| Water | 4.28 | Turbid | 13,541 |
| LOQ (quantitative detection limit) | | | LOQ = 0.0003 mg/mL, S/N = 22 |

The result showed that the amorphous form solid of the compound was easily soluble in a hydrochloric acid solution, an acetate buffer solution and water, and was slightly soluble or insoluble in a phosphate buffer solution.

4. Hygroscopicity Test of Amorphous Form Sample of Compound Represented by Formula (II)

A hygroscopicity of an amorphous form sample was detected. (The hygroscopicity of the compound was determined according to the method in the General Rules of the Chinese Pharmacopoeia (2015 Version) Volume IV).

Three dry glass weighing bottles with stoppers were weighed, the results of which were recorded as $m_1$ 1, $m_1$ 2 and $m_1$ 3. An appropriate amount of crude drug sample was spread in the weighed weighing bottles (the sample has a thickness of about 1 mm), then accurately weighed and recorded as $m_2$ 1, $m_2$ 2 and $m_2$ 3. The weighing bottles were open and placed together with bottle caps in a dryer with saturated ammonium chloride solution at a lower part, the dryer was covered, then the dryer was placed in a thermostat at 25° C. for 24 h. After being placed for 24 h, the weighing bottles were covered, then taken out for accurate weighing, the results of which were recorded as $m_3$ 1, $m_3$ 2 and $m_3$ 3. Weight increase by hygroscopicity was calculated, and the calculation formula was as follows: weight increase percentage=$100\% \times (m_3-m_2)/(m_2-m_1)$. (A hygroscopicity result was shown in Table 5).

TABLE 5

Hygroscopicity Result of Amorphous Form Sample of Compound Represented by Formula (II)

| Batch No. of sample | $m_1$ (mg) | $m_2$ (mg) | $m_3$ (mg) | Weight increase percentage (%) | Average value (%) |
|---|---|---|---|---|---|
| 1 | 34106.47 | 35042.38 | 35086.50 | 4.714 | 5.24 |
| 2 | 33971.43 | 34826.02 | 34875.50 | 5.790 | |
| 3 | 35198.49 | 36030.94 | 36074.35 | 5.215 | |

Experimental conclusion: according to the hygroscopicity test result, an average weight increase of hygroscopicity of the amorphous form sample was 5.24%, which was less than 15% but not less than 2%, and the compound had hygroscopicity.

Drug Metabolism Experiment

Experimental Purpose:

Through the experiment of drug metabolism in a mouse, the metabolism of the compound in the mouse is evaluated by taking $C_{max}$, $t_{1/2}$, AUC, MRT and B/P ratio in vivo as indexes.

1. Pharmacokinetic study of parent compound A and prodrug B thereof (the specific structures were represented by formulas A and B) intramuscularly injected in mouse A test compound was mixed with an appropriate amount of sesame oil, and the mixture was vortexed and ultrasonically processed to obtain an even suspension of 25 μmol/mL. A SD mouse aged 6 weeks to 9 weeks (Shanghai SLAC Laboratory Animal Co., Ltd) was selected and intramuscularly injected with a suspension of the test compound at a dose of 20 μmol/kg or 40 μmol/kg. Whole blood of a certain period of time was collected, and a precipitant (acetonitrile, methanol and internal standard for analysis) was added and centrifuged. A supernatant solution was analyzed for a drug concentration by a LC-MS/MS method (if the test drug was the prodrug, concentrations of the prodrug and the hydrolyzed parent drug were analyzed simultaneously), and pharmacokinetic parameters were calculated by Phoenix WinNonlin software (Pharsight Company of the United States).

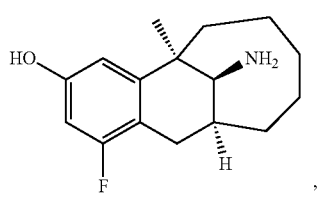

A

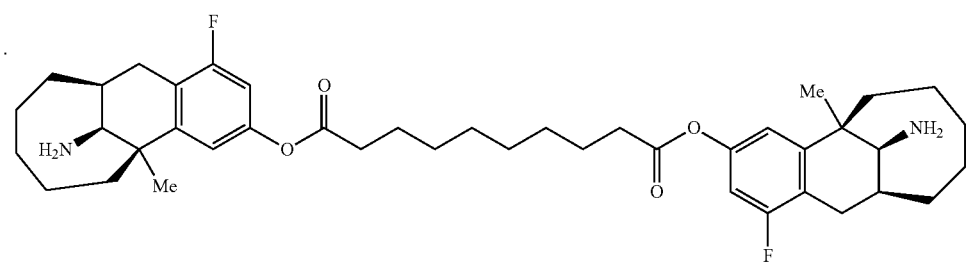

B

TABLE 6

Pharmacokinetic Experiment Result of Intramuscular Injection of Carboxylate Diester Prodrug of Compound A

| Compound No. | Compound B | Compound B Parent compound A |
|---|---|---|
| $C_{max}$ (nM) | ND | 192 |
| $T_{max}$ (hr) | ND | 2.17 |
| $t_{1/2}$ (hr) | ND | 33.7 |
| $AUC_{0\text{-}last}$ (nM · hr) | ND | 3235 |
| $MRT_0$-last (hr) | ND | 18.0 |

Note: the dosage of all the compounds was 20 μmol/kg. Each 20 μmol of the carboxylate diester prodrug could theoretically hydrolyze to produce 40 μmol of active components of a compound 21.

ND=not determined (parameters could not be determined because an end eliminated phase could not be fully defined)

Compound A was free alkali of the compound 1-16 before salt formation

Compound B is free alkali of the compound represented by formula (II) before salt formation The pharmacokinetic experiment result of the intramuscular injection proves that a sesame oil suspension of the carboxylate diester prodrug of the compound A is slowly released in vivo after intramuscular injection and quickly hydrolyzed into the parent drug compound A, which can significantly prolong a retention time of the parent drug compound A in the mouse and reduce $C_{max}$, thus achieving the purpose of prolonging a drug action time and improving the safety.

What is claimed is:

1. An amorphous form of a compound represented by formula (II), (II)

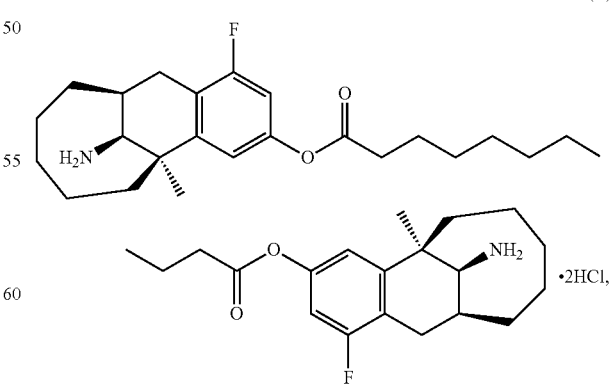

·2HCl, wherein an X-ray powder diffraction spectrum of the amorphous form is shown in FIG. 1.

2. The amorphous form according to claim 1, wherein a MDSC curve of the amorphous form undergoes glass transition at 79.07° C.±3° C.

3. The amorphous form according to claim 2, wherein the MDSC curve of the amorphous form is shown in FIG. 2.

4. The amorphous form according to claim 1, wherein at 120.00° C. of a TGA curve of the amorphous form, a weight is reduced by 4.270%; and at 199.60° C.±3° C. of the TGA curve of the amorphous form, the weight is reduced by 5.1553%.

5. The amorphous form according to claim 4, wherein the TGA curve of the amorphous form is shown in FIG. 3.

* * * * *